United States Patent
Suzuki

(10) Patent No.: US 9,186,305 B1
(45) Date of Patent: Nov. 17, 2015

(54) SUNSCREEN PRODUCTS IN WHICH EXCESSIVE WHITENESS DUE TO TITANIUM DIOXIDE AND ZINC OXIDE IS VISUALLY MASKED UPON SKIN APPLICATION

(71) Applicant: Daisuke Suzuki, Yokohama (JP)

(72) Inventor: Daisuke Suzuki, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 44 days.

(21) Appl. No.: 14/280,983

(22) Filed: May 19, 2014

(51) Int. Cl.
*A61K 8/11* (2006.01)
*A61K 8/06* (2006.01)
*A61K 8/29* (2006.01)
*A61K 8/27* (2006.01)
*A61Q 17/04* (2006.01)

(52) U.S. Cl.
CPC . *A61K 8/11* (2013.01); *A61K 8/064* (2013.01); *A61K 8/27* (2013.01); *A61K 8/29* (2013.01); *A61Q 17/04* (2013.01); *A61K 2800/20* (2013.01); *A61K 2800/56* (2013.01)

(58) Field of Classification Search
CPC ........... A61K 8/11; A61K 8/064; A61K 8/29; A61K 8/27; A61K 2800/56; A61K 2800/20; A61Q 17/04
See application file for complete search history.

(56) References Cited

U.S. PATENT DOCUMENTS 7,368,105 B2 * 5/2008 Candau .................... A61K 8/35
424/400

2009/0017081 A1 * 1/2009 Takakura ............... A61K 8/064
424/401
2011/0165208 A1 * 7/2011 Kim ..................... A61K 8/0283
424/401
2014/0205552 A1 7/2014 Fukuhara

FOREIGN PATENT DOCUMENTS

WO 2013/031374 A1 3/2013
WO 2013/107350 A1 7/2013

OTHER PUBLICATIONS

The website "http://www.dr-straetmans.de/en/products/productdescription_symbiomuls_gc.php" printed on May 15, 2014.
International Search Report issued for PCT Patent Application No. PCT/JP2015/002486, which claims priority to U.S. Appl. No. 14/280,983, mailed on Aug. 18, 2015, 12 pages.

* cited by examiner

*Primary Examiner* — Blessing M Fubara

(57) ABSTRACT

Sunscreen products that do not require the use of organic, ultraviolet-absorbing agents are provided. Effective protection of the skin from ultraviolet light is attained by increasing the amounts of titanium dioxide and zinc oxide. To mask the excessive whiteness that would otherwise result from the oxides, the sunscreen products contain multilayer-type encapsulations containing pigments. Before use, the pigments are enveloped in capsules that muffle the pigments' color. When the sunscreen product is applied to the skin, the capsules break and the pigments are released to counter the excessive whiteness due to titanium dioxide and zinc oxide. Sunscreen product precursors, from which these sunscreen products can be generated by stirring, are also provided. A sunscreen product package contains the sunscreen product precursor and a stirring ball. A method of ultraviolet protection is provided by shaking the sunscreen product package and applying the sunscreen product thus generated to the skin.

64 Claims, 3 Drawing Sheets
(3 of 3 Drawing Sheet(s) Filed in Color)

SUNSCREEN PRODUCTS IN WHICH EXCESSIVE WHITENESS DUE TO TITANIUM DIOXIDE AND ZINC OXIDE IS VISUALLY MASKED UPON SKIN APPLICATION

FIELD OF THE INVENTION

The present invention generally relates to sunscreen products that contain titanium dioxide and zinc oxide to provide protection to skin from ultraviolet light. These products do not require (though they may contain) organic, ultraviolet-absorbing agents for effective ultraviolet protection, and yet exhibit colors attractive to users of the products both in their pre-application state and after application to the skin. In addition, the present invention generally relates to precursors of these sunscreen products. The sunscreen product may be generated by stirring or agitating the precursor. The present invention further relates generally to methods of protecting human skin from ultraviolet light by applying the sunscreen product to the skin, or by generating the sunscreen product from the precursor and applying it to the skin.

BACKGROUND OF THE INVENTION

Conventional sunscreen products contain ultraviolet-absorbing agents, ultraviolet-scattering agents, or both, so that they may achieve desirable levels and effects of protecting the skin from ultraviolet light. Ultraviolet-absorbing agents are usually organic compounds, such as ethylhexyl methoxycinnamate and octocrylene. On the other hand, ultraviolet-scattering agents include inorganic, powder components, such as titanium dioxide and zinc oxide.

There also exists a category of products called "non-chemical sunscreens." These sunscreen products are intended to exert the effects of protecting the skin from ultraviolet light by containing inorganic, ultraviolet-scattering agents, but not organic, ultraviolet-absorbing agents. This is because these organic, ultraviolet-absorbing agents are apt to irritate or sensitize the skin of a user.

In order to achieve desirable levels and effects of ultraviolet protection or exhibit satisfactory values of Sun Protection Factor ("SPF"), these non-chemical sunscreen products must contain an increased amount of inorganic, powder components such as titanium dioxide and zinc oxide so that they can compensate for the absence of organic, ultraviolet-absorbing agents. When a sunscreen product contains these inorganic, powder components in an increased amount, however, the product appears excessively white to the eye. While a product appearing excessively white in its pre-application state may not be problematic, the sunscreen product will not be attractive to a user if such excessive whiteness remains and lingers on even after the product is applied to the skin. In fact, the issue of excessive whiteness arises whenever an elevated amount of titanium dioxide, zinc oxide, or both is used, regardless of the presence or absence of organic, ultraviolet-absorbing agents in the product. The issue of excessive whiteness is thus not limited to non-chemical sunscreens.

Further, while pigments may be added to a non-chemical sunscreen product to suppress or mask the appearance of excessive whiteness, pigments that impart natural-looking color to the product post-application (i.e., when it is spread out on the skin) tend to make the color of the product in its pre-application state (i.e., in bulk) unattractive to the user. For example, pigments that make the product look pale yellow with a tinge of pink upon application to the skin actually make the product itself appear brown. Although a user may not mind applying such a product to parts of the body that are usually hidden from view (such as one's buttocks), the user is not likely to feel encouraged or tempted to apply it on the face, even if the user is told that the product will appear pale yellow with a tinge of pink when spread out on the skin. In addition, due to the thick color, a user may feel as if she or he were putting makeup or foundation on rather than applying a sunscreen product.

BRIEF SUMMARY OF THE INVENTION

One aspect of the present invention relates to sunscreen products that contain multilayer-type encapsulations containing pigments. These multilayer-type encapsulations remain intact within a sunscreen product before the product is applied to the skin, thereby reducing or hiding the visual effects of a pigment's color to the eye. When the product is applied to the skin, however, the encapsulations are broken by the force exerted during strokes of application (for example, by the palm of a hand or fingers), and the pigments are released and spread out over the skin to compensate for or visually override the excessive whiteness that may arise from the inorganic, powder components. This allows one to reduce or eliminate the use of organic, ultraviolet-absorbing agents in a sunscreen product while achieving desirable ultraviolet-protection effects by increasing the use of inorganic, ultraviolet-scattering agents, but without degrading the appearance of the product itself before use or the appearance of the product after it is applied to the skin.

Another aspect of the present invention relates to precursors of the sunscreen products just described. For example, a precursor may be a mixture of two phases separated on a macroscopic scale in a container, in which the upper layer is an oil phase and the lower layer is an aqueous phase. Titanium dioxide, zinc oxide, and multilayer-type encapsulations containing pigments may be in either phase. The container may further hold inside a stirring ball or a stirring object, and right before use, the precursor may be stirred and mixed by manually shaking the container to move the stirring ball or object around, thereby producing a water-in-oil-emulsion-type solution, which is then applied to the skin. Similar stirring and mixing effects may be achieved by simply shaking the container if there is no stirring object inside but sufficient free space is available within the container, or by inserting a stick or an elongated object from the outside and actively agitating the mixture. While the multilayer-type encapsulations containing pigments break apart when manually applied to the skin, the inventor of the present invention has discovered that they remain intact when the precursor is manually stirred and mixed.

Yet another aspect of the present invention relates to methods of protecting the skin from ultraviolet light by applying a sunscreen product described above, or by preparing a sunscreen product from its precursor as described above and then applying it to the skin.

The headings used in this disclosure are for organizational purposes only and are not meant to limit the scope of the description. As used throughout this disclosure, the words "may" and "can" are used in a permissive sense (i.e., meaning "having the potential to"), rather than in a mandatory sense (i.e., meaning "must"). Similarly, the words "include," "including," and "includes" mean "including but not limited to."

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

The features and advantages of the present invention will be more fully understood with reference to the detailed description in the next section when taken in conjunction with the following figures.

FIG. 1A shows the comparative sunscreen product before it is spread out on the skin, and FIG. 1B shows the comparative sunscreen product after it has been spread out on the skin.

FIG. 2A shows the comparative sunscreen product in bulk, that is, before it is applied to the skin, and FIG. 2B shows the comparative sunscreen product after it has been spread out on the skin.

FIG. 3A shows the inventive sunscreen product before it is spread out on the skin, and FIG. 3B shows the inventive sunscreen product after it has been spread out on the skin.

DETAILED DESCRIPTION OF THE INVENTION

The detailed description that follows generally describes various exemplary embodiments of the present invention, and should not be considered to be exclusive of other equally effective embodiments, as would be understood by those of ordinary skill in the art. Further, numerous specific details are given in order to provide a thorough understanding of the embodiments and other examples. In some instances, however, well-known methods, procedures, and components have not been described in detail, so as to not obscure the following description. The embodiments and examples disclosed are for exemplary purposes only. Other embodiments and examples may be employed in lieu of, or in combination with, the embodiments and examples disclosed.

The sunscreen products of the present invention may be of water-in-oil-emulsion types, of single-oil-phase types, or of other types. As described below, they contain multilayer-type encapsulations that contain pigments, and titanium dioxide powder and zinc oxide powder whose surface has been treated or processed to be hydrophobic. They may also exhibit low viscosity, such as 10,000 mPa·s or less at 30° C., and may further exhibit SPF of certain values, such as 40 or more.

The sunscreen product precursors of the present invention are mixtures of a plurality of phases separated on a macroscopic scale, which are capable of producing the sunscreen products mentioned above, for example, those of water-in-oil-emulsion types, when physically stirred or agitated.

The methods of protecting the skin from ultraviolet light of the present invention involve applying a sunscreen product mentioned above to the skin, or stirring or agitating a sunscreen product precursor mentioned above to prepare a sunscreen product and applying that product to the skin.

Figure 1A:
FIGS. 1A and 1B are color photographs of a comparative sunscreen product that contains 5 weight % of hydrophobized titanium dioxide and 25 weight % of hydrophobized zinc oxide, but no organic, ultraviolet-absorbing agents, no naked pigments, and no multilayer-type encapsulations containing pigments. (This is Comparative Example 4 later on.)
Figure 1B:
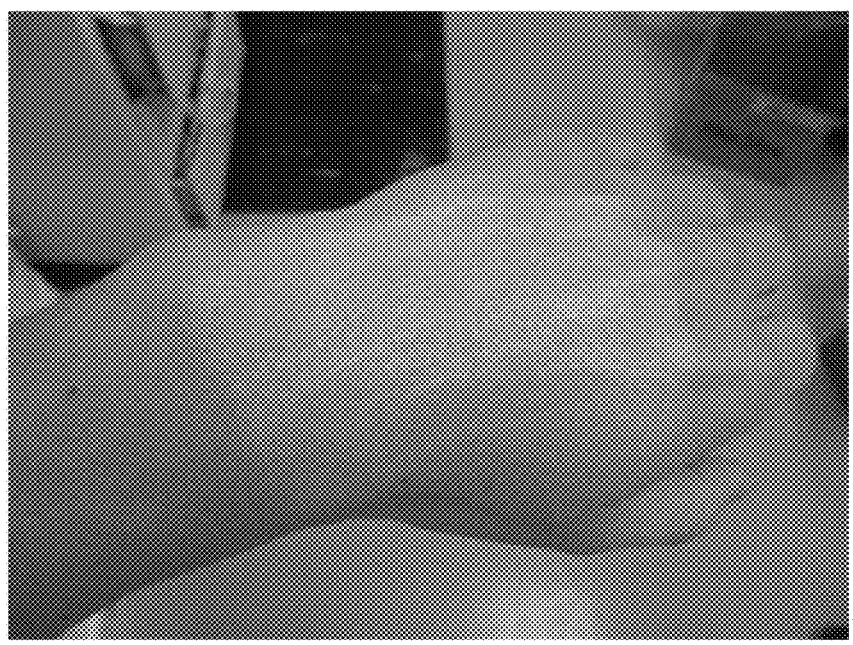

FIGS. 1A and 1B are color photographs of a comparative sunscreen product that contains 5 weight % of hydrophobized titanium dioxide and 25 weight % of hydrophobized zinc oxide, but no organic, ultraviolet-absorbing agents, no naked pigments, and no multilayer-type encapsulations containing pigments. FIG. 1A shows the comparative sunscreen product before it is spread out on the skin, and FIG. 1B shows the comparative sunscreen product after it has been spread out on the skin. The weight percentages of the hydrophobized titanium dioxide and zinc oxide are chosen so that the comparative sunscreen product will have a desirable level of ultraviolet-protection effects. While a user may not mind the whiteness appearing in FIG. 1A before spreading it out on the skin, the excessive whiteness that remains or lingers on after spreading it out on the skin as shown in FIG. 1B will not be attractive to the user.

Figure 2A:
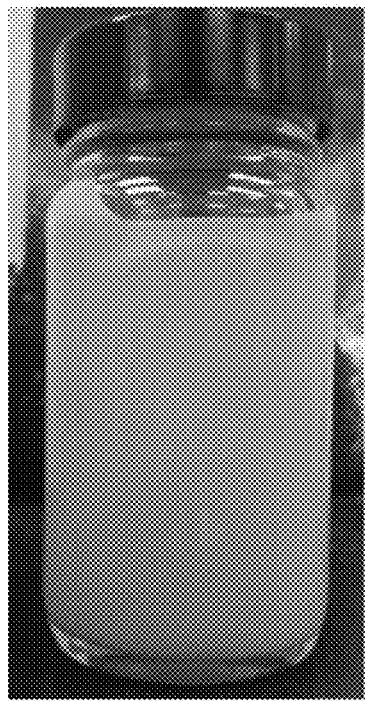
FIGS. 2A and 2B are color photographs of a comparative sunscreen product that contains 5 weight % of hydrophobized titanium dioxide, 25 weight % of hydrophobized zinc oxide, 0.048 weight % of Unipure Red LC 381 LL (i.e., naked red pigment), and 0.096 weight % of Unipure Yellow LC 182 LL (i.e., naked yellow pigment), but no organic, ultraviolet-absorbing agents and no multilayer-type encapsulations containing pigments. (This is Comparative Example 3 later on.)
Figure 2B:

FIGS. 2A and 2B are color photographs of a comparative sunscreen product that contains 5 weight % of hydrophobized titanium dioxide, 25 weight % of hydrophobized zinc oxide, 0.048 weight % of Unipure Red LC 381 LL (i.e., naked red pigment), and 0.096 weight % of Unipure Yellow LC 182 LL (i.e., naked yellow pigment), but no organic, ultraviolet-absorbing agents and no multilayer-type encapsulations containing pigments. FIG. 2A shows the comparative sunscreen product in bulk, that is, before it is applied to the skin, and FIG. 2B shows the comparative sunscreen product after it has been spread out on the skin. The weight percentages of the naked red and yellow pigments are chosen so that the excessive whiteness that would otherwise appear is masked when it is applied to the skin as shown in FIG. 2B. However, when such an adjustment is made, the color of the comparative sunscreen product in bulk, that is, before use, ends up being too thick, and thus unattractive to a user, as shown in FIG. 2A.

Figure 3A:
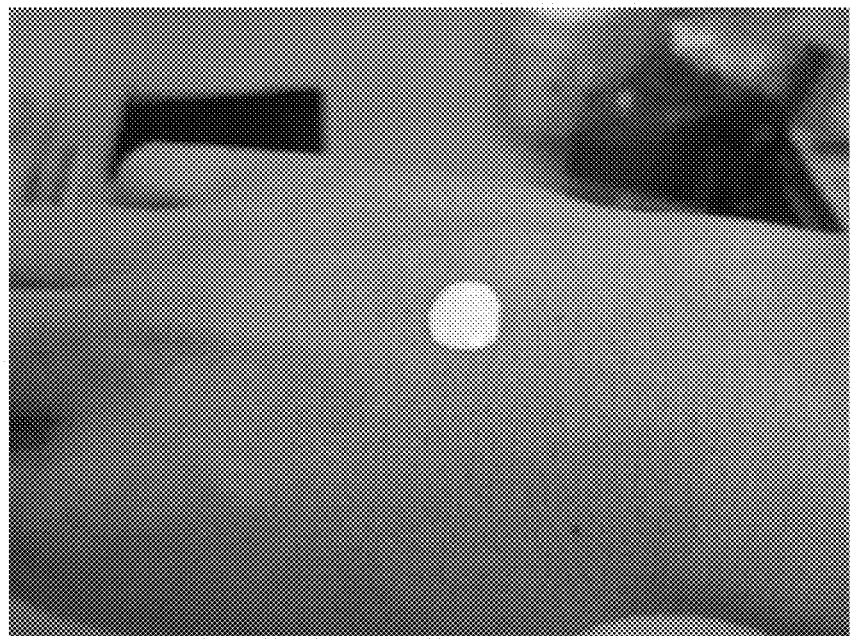
FIGS. 3A and 3B are color photographs of a sunscreen product of the present invention, which contains 5 weight % of hydrophobized titanium dioxide, 25 weight % of hydrophobized zinc oxide, 0.2 weight % of MAGICOLOR® 103RP (which contains red pigment), and 0.4 weight % of MAGICOLOR® 103YP (which contains yellow pigment), but no organic, ultraviolet-absorbing agents and no naked pigments. (This is Practice Example 3 later on.)
Figure 3B:

Finally, FIGS. 3A and 3B are color photographs of a sunscreen product of the present invention, which contains 5 weight % of hydrophobized titanium dioxide, 25 weight % of hydrophobized zinc oxide, 0.2 weight % of MAGICOLOR® 103RP (which contains red pigment), and 0.4 weight % of MAGICOLOR® 103YP (which contains yellow pigment), but no organic, ultraviolet-absorbing agents and no naked pigments. MAGICOLOR® 103RP and 103YP refer to certain commercial products of multilayer-type encapsulations containing pigments. FIG. 3A shows the inventive sunscreen product before it is spread out on the skin, and FIG. 3B shows the inventive sunscreen product after it has been spread out on the skin. The sunscreen product of the present invention does not exhibit a thick color in bulk, that is, before use, that may be unattractive to a user, as shown in FIG. 3A. And yet, it is able to mask the excessive whiteness that would otherwise appear and to impart a natural-looking color when spread out on the skin as shown in FIG. 3B.

(1) Water-in-Oil-Emulsion-Type Sunscreen Products

Conventional water-in-oil-emulsion-type sunscreen products may be used as the bases of the sunscreen products of the present invention, as long as they are compatible with the multilayer-type encapsulations containing pigments that are to be added. Water-in-oil emulsions commonly refer to mixtures of water and one or more kinds of oil in which aqueous droplets of less than macroscopic sizes are dispersed in the oil.

Substances that may form the solvent of the oil phase of a water-in-oil-emulsion-type sunscreen product include decamethyl cyclopentasiloxane, isononyl isononanoate, dimethyl polysiloxane, heptamethyl octyl trisiloxane, trimethylsiloxysilicate, liquid paraffin, squalane, avocado oil, macadamia nut oil, corn oil, olive oil, canola oil, evening primrose oil, castor oil, sunflower seed oil, tea oil, rice bran oil, jojoba oil, cacao butter, palm oil, squalene, beef tallow, japan wax, bees wax, candelilla wax, carnauba wax, spermaceti, lanolin, polyoxyethylene (8 mol) oleyl alcohol ether, glyceryl monooleate, cyclomethicone, diphenyl polysiloxane, isodecane, isododecane, and isohexadecane. Commonly used among these are decamethyl cyclopentasiloxane, dimethyl polysiloxane, liquid paraffin, and isododecane. These substances may be used as the solvent of the oil phase of a water-in-oil-emulsion-type sunscreen product of the present invention, as long as they are compatible with the multilayer-type encapsulations containing pigments that are to be added.

Water may be contained in conventional water-in-oil-emulsion-type sunscreen products in an amount ranging between 0.01 weight % inclusive and 98 weight % inclusive, preferably between 1 weight % inclusive and 60 weight % inclusive, more preferably between 3 weight % inclusive and 40 weight % inclusive, and most preferably between 5 weight % inclusive and 25 weight % inclusive, relative to the total amount of the water-in-oil-emulsion-type sunscreen product. The same applies to the water-in-oil-emulsion-type sunscreen products of the present invention. Generally, the less water the product contains, the lower its viscosity becomes.

The oil phase of conventional water-in-oil-emulsion-type sunscreen products usually contains organic, ultraviolet-absorbing agents and inorganic, ultraviolet-scattering agents, in which the surface of the inorganic, ultraviolet-scattering agents has been treated or processed to be hydrophobic. Although the water-in-oil-emulsion-type sunscreen products of the present invention require the use of hydrophobized, inorganic, ultraviolet-scattering agents, they do not require the use of organic, ultraviolet-absorbing agents.

Optionally, conventional water-in-oil-emulsion-type sunscreen products may also contain other powder ingredients, liquid fats and oils, solid fats and oils, waxes, hydrocarbon oils, higher fatty acids, higher alcohols, ester oils, silicone oils, anionic surfactants, cationic surfactants, ampholytic surfactants, hydrophilic nonionic surfactants, lipophilic surfactants, humectants, natural water-soluble polymers, semisynthetic water-soluble polymers, synthetic water-soluble polymers, thickeners, metal ion sequestering agents, lower alcohols, polyhydric alcohols, monosaccharides, oligosaccharides, polysaccharides, amino acids, amino acid derivatives, organic amines, polymer emulsions, pH adjusting agents, vitamins, antioxidants, antioxidation assistants, and other possible ingredients, including skin nutrients and perfumes. Examples of these optional ingredients are described below. The water-in-oil-emulsion-type sunscreen products of the present invention may contain any of these optional ingredients, as long as they are compatible with the multilayer-type encapsulations containing pigments that are to be added.

(A) Organic, Ultraviolet-Absorbing Agents

Examples of organic, ultraviolet-absorbing agents include para-aminobenzoic acid ("PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, homo mentyl-N-acetyl anthranilate, amyl salicylate, mentyl salicylate, homo mentyl salicylate, octyl salicylate, phenyl salicylate, benzyl salicylate, p-isopropanol phenyl salicylate, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate, 2-ethylhexyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethyl hexanoyl-di-p-methoxy cinnamate, bis-resorcinol triazine (e.g., bis{[4-(2-ethylhexyloxy)-2-hydroxy]phenyl}-6-(4-methoxyphenyl)-1,3,5-triazine), 2,4,6-tris[4-(2-ethylhexyloxycarbonyl)aniline]-1,3,5-triazine, 3-(4'-methylbenzylidene)-d-1-camphor, 3-benzylidene-d-1-camphor, 2-phenyl-5-methyl benzoxazole, 2,2'-hydroxy-5-methylphenyl benzotriazol, 2-(2'-hydroxy-5'-t-octylphenyl)benzotriazol, 2-(2'-hydroxy-5'-methylphenyl)benzotriazol, dibenzaladine, dianisoylmethane, 4-methoxy-4'-t-butyl dibenzoyl-methane, 5-(3,3-dimethyl-2-norbornylidene)-3-pentane-2-one, and dimorpholinopyridazinone.

The water-in-oil-emulsion-type sunscreen products of the present invention may contain organic, ultraviolet-absorbing agents in no detectable amount, in an amount of no more than 3 weight %, in an amount of no more than 5 weight %, or in an amount of no more than 10 weight %, relative to the total weight of the sunscreen product, as long as the organic, ultraviolet-absorbing agents are compatible with the multilayer-type encapsulations containing pigments that are used.

(B) Other Powder Ingredients

Examples of other powder ingredients include: inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, myristic acid zinc, calcium palmitate, and aluminum stearate), and boron nitride); and organic powders (for example, polyamide resin powder (nylon powder), polyethylene powder, poly-methyl methacrylate powder, polystyrene powder, powders of the copolymer resin of styrene and acrylic acid, benzoguanamine resin powder, polytetrafluoroethylene powder, and cellulose powder).

(C) Liquid Fats and Oils

Examples of liquid fats and oils include avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerin.

(D) Solid Fats and Oils Examples of solid fats and oils include cacao butter, coconut oil, hydrogenated coconut oil, palm oil, palm kernel oil, Japanese core wax nucleus oil, hydrogenated oil, Japanese core wax, and hydrogenated castor oil.

(E) Waxes Examples of waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

(F) Hydrocarbon Oils

Examples of hydrocarbon oils include liquid petrolatum, ozocerite, squalane, pristane, paraffin, ceresin, squalene, petrolatum, and microcrystalline wax.

(G) Higher Fatty Acids

Examples of higher fatty acids include lauric acid, myristic acid, palmitic acid, stearic acid, behenic acid, oleic acid, undecylenic acid, tall oil fatty acid, isostearic acid, linolic acid, linoleic acid, eicosapentaenoic acid (EPA), and docosahexaenoic acid (DHA).

(H) Higher Alcohols

Examples of higher alcohols include straight-chain alcohols (for example, lauryl alcohol, cetyl alcohol, stearyl alcohol, behenyl alcohol, myristyl alcohol, oleyl alcohol, and cetostearyl alcohol) and branched-chain alcohols (for example, mono stearyl glycerin ether (batyl alcohol), 2-decyltetradecynol, lanolin alcohol, cholesterol, phytosterol, hexyl dodecanol, isostearyl alcohol, and octyl dodecanol).

(I) Ester Oils

Examples of ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, isocetyl stearate, isocetyl isostearate, cholesteryl 12-hydroxystearate, di-2-ethylene glycol ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethyl hexanoate, trimethylolpropane triisostearate, tetra-2-pentaerythritol ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

(J) Silicone Oils

Examples of silicone oils include: chain-type polysiloxanes (for example, dimethylpolysiloxane, methylphenyl polysiloxane, and diphenyl polysiloxane); ring-type polysiloxanes (for example, octamethylcyclotetrasiloxane, decamethyl cyclopentasiloxane, and dodecamethyl cyclohexasiloxane); silicone resins forming a three-dimensional network structure; silicone rubbers; and various modified polysiloxanes (for example, amino-modified polysiloxanes, polyether-modified polysiloxanes, alkyl-modified polysiloxanes, and fluorine-modified polysiloxanes).

(K) Anionic Surfactants

Examples of anionic surfactants include: fatty acid soaps (for example, sodium laurate and sodium palmitate); higher alkyl sulfuric ester salts (for example, sodium lauryl sulfate and potassium lauryl sulfate); alkylether sulfuric ester salts (for example, POE-triethanolamine lauryl sulfate and sodium POE-lauryl sulfate); N-acyl sarcosinic acids (for example, sodium N-lauroyl sarcosinate); higher fatty acid amide sulfonic acid salts (for example, sodium N-myristoyl N-methyl taurate, sodium cocoyl methyl taurate, and sodium laurylmethyl taurate); phosphoric ester salts (for example, sodium POE-oleyl ether phosphate and POE stearyl ether phosphoric acid); sulfosuccinates (for example, sodium di-2-ethylhexylsulfosuccinate, sodium monolauroyl monoethanol amide polyoxyethylene sulfosuccinate, and sodium lauryl polypropylene glycol sulfosuccinate); alkyl benzene sulfonates (for example, sodium linear dodecyl benzene sulfonate, triethanolamine linear dodecyl benzene sulfonate, and linear dodecyl benzene sulfonic acid); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and sodium N-myristoyl-L-glutamate); sulfated oils (for example, turkey red oil); POE-alkylether carboxylic acid; POE-alkylarylether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium caseinate.

(L) Cationic Surfactants

Examples of cationic surfactants include alkyltrimethylammonium salts (for example, stearyltrimethyl ammonium chloride and lauryltrimethyl ammonium chloride); alkylpyridinium salts (for example, cetylpyridinium chloride); distearyldimethylammonium chloride dialkyldimethylammonium salt; poly(N,N'-dimethyl-3-methylene piperidinium) chloride; alkyl quaternary ammonium salts; alkyl dimethylbenzyl ammonium salts; alkyl isoquinolinium salts; dialkylmorpholine salts; POE alkyl amines; alkyl amine salts; polyamine fatty acid derivatives; amylalcohol fatty acid derivatives; benzalkonium chloride; and benzethonium chloride.

(M) Ampholytic Surfactants

Examples of ampholytic surfactants include: imidazoline-type ampholytic surfactants (for example, 2-undecyl-N,N,N-(hydroxyethyl carboxymethyl)-2-imidazoline sodium salt and 2-cocoyl-2-imidazolinium hydroxidel-carboxyethyloxy 2 sodium salt); and betaine-type surfactants (for example, 2-heptadecyl-n-carboxymethyl-n-hydroxyethyl imidazolinium betaine, lauryldimethylaminoacetic acid betaine, alkyl betaine, amide betaine, and sulfobetaine).

(N) Hydrophilic Nonionic Surfactants

Examples of hydrophilic nonionic surfactants include: polyglycerin fatty acid esters (for example, hexaglyceryl monolaurate (HLB 14.5), hexaglyceryl monomyristate (HLB 11), hexaglyceryl monostearate (HLB 9.0), hexaglyceryl monooleate (HLB 9.0), decaglyceryl monolaurate (HLB 15.5), decaglyceryl monomyristate (HLB 14.0), decaglyceryl monostearate (HLB 12.0), decaglyceryl monoisostearate (HLB 12.0), decaglyceryl monooleate (HLB 12.0), decaglyceryl distearate (HLB 9.5), and decaglyceryl diisostearate (HLB 10.0)); polyoxyethylene glycerin fatty acid esters (for example, polyoxyethylene ("POE") (5) glyceryl monostearate (HLB 9.5), POE (15) glyceryl monostearate (HLB 13.5), POE (5) glyceryl monooleate (HLB 9.5), and POE (15) glyceryl monooleate (HLB 14.5)); polyoxyethylene sorbitan fatty acid esters (for example, POE (20) sorbitan monococoate (HLB 16.9), POE (20) sorbitan monopalmitate (HLB 15.6), POE (20) sorbitan monostearate (HLB 14.9), POE (6) sorbitan monostearate (HLB 9.5), POE (20) sorbitan tristearate (HLB 10.5), POE (20) sorbitan monoisostearate (HLB 15.0), POE (20) sorbitan monooleate (HLB 15.0), POE (6) sorbitan monooleate (HLB 10.0), and POE (20) sorbitan trioleate (HLB 11.0)); polyoxyethylene sorbit fatty acid esters (for example, POE (6) sorbit monolaurate (HLB 15.5), POE (60) sorbit tetrastearate (HLB 13.0), POE (30) sorbit tetraoleate (HLB 11.5), POE (40) sorbit tetraoleate (HLB 12.5), and POE (60) sorbit tetraoleate (HLB 14.0)); polyoxyethylene lanolin/lanolin alcohol/beeswax derivatives (for example, POE (10) lanolin (HLB 12.0), POE (20) lanolin (HLB 13.0), POE (30) lanolin (HLB 15.0), POE (5) lanolin alcohol (HLB 12.5), POE (10) lanolin alcohol (HLB 15.5), POE (20) lanolin alcohol (HLB 16.0), POE (40) lanolin alcohol (HLB 17.0), and POE (20) sorbit beeswax (HLB 9.5)); polyoxyethylene castor oils/hydrogenated oils (for example, POE (20) castor oil (HLB 10.5), POE (40) castor oil (HLB 12.5), POE (50) castor oil (HLB 14.0), POE (60) castor oil (HLB 14.0), POE

(20) hydrogenated castor oil (HLB 10.5), POE (30) hydrogenated castor oil (HLB 11.0), POE (40) hydrogenated castor oil (HLB 13.5), POE (60) hydrogenated castor oil (HLB 14.0), POE (80) hydrogenated castor oil (HLB 16.5), and POE (100) hydrogenated castor oil (HLB 16.5)); polyoxyethylene sterols/hydrogenated sterols (for example, POE (5) phytosterol (HLB 9.5), POE (10) phytosterol (HLB 12.5), POE (20) phytosterol (HLB 15.5), POE (30) phytosterol (HLB 18.0), POE (25) phytostanol (HLB 14.5), and POE (30) cholestanol (HLB 17.0)); polyoxyethylene alkyl ethers (for example, POE (2) lauryl ether (HLB 9.5), POE (4.2) lauryl ether (HLB 11.5), POE (9) lauryl ether (HLB 14.5), POE (5.5) cetyl ether (HLB 10.5), POE (7) cetyl ether (HLB 11.5), POE (10) cetyl ether (HLB 13.5), POE (15) cetyl ether (HLB 15.5), POE (20) cetyl ether (HLB 17.0), POE (23) cetyl ether (HLB 18.0), POE (4) stearyl ether (HLB 9.0), POE (20) stearyl ether (HLB 18.0), POE (7) oleyl ether (HLB 10.5), POE (10) oleyl ether (HLB 14.5), POE (15) oleyl ether (HLB 16.0), POE (20) oleyl ether (HLB 17.0), POE (50) oleyl ether (HLB 18.0), POE (10) behenyl ether (HLB 10.0), POE (20) behenyl ether (HLB 16.5), POE (30) behenyl ether (HLB 18.0), POE (2) ($C_{12-15}$) alkyl ether (HLB 9.0), POE (4) ($C_{12-15}$) alkyl ether (HLB 10.5), POE (10) ($C_{12-15}$) alkyl ether (HLB 15.5), POE (5) secondary alkyl ether (HLB 10.5), POE (7) secondary alkyl ether (HLB 12.0), POE (9) alkyl ether (HLB 13.5), and POE (12) alkyl ether (HLB 14.5)); polyoxyethylene polyoxypropylene alkyl ethers (for example, POE (1) polyoxypropylene ("POP") (4) cetyl ether (HLB 9.5), POE (10) POP (4) cetyl ether (HLB 10.5), POE (20) POP (8) cetyl ether (HLB 12.5), POE (20) POP (6) decyltetradecyl ether (HLB 11.0), and POE (30) POP (6) decyltetradecyl ether (HLB 12.0)); polyethylene glycol fatty acid esters (for example, polyethylene glycol ("PEG") (10) (HLB 12.5), PEG (10) monostearate (HLB 11.0), PEG (25) monostearate (HLB 15.0), PEG (40) monostearate (HLB 17.5), PEG (45) monostearate (HLB 18.0), PEG (55) monostearate (HLB 18.0), PEG (10) monooleate (HLB 11.0), PEG distearate (HLB 16.5), and PEG diisostearate (HLB 9.5)); and polyoxyethylene glyceryl isostearates (for example, PEG (8) glyceryl isostearate (HLB 10.0), PEG (10) glyceryl isostearate (HLB 10.0), PEG (15) glyceryl isostearate (HLB 12.0), PEG (20) glyceryl isostearate (HLB 13.0), PEG (25) glyceryl isostearate (HLB 14.0), PEG (30) glyceryl isostearate (HLB 15.0), PEG (40) glyceryl isostearate (HLB 15.0), PEG (50) glyceryl isostearate (HLB 16.0), and PEG (60) glyceryl isostearate (HLB 16.0)).

(O) Lipophilic Surfactants

Examples of lipophilic surfactants include POE (2) stearyl ether (HLB 4.0), self-emulsified propylene glycol monostearate (HLB 4.0), glyceryl myristate (HLB 3.5), glyceryl monostearate (HLB 4.0), self-emulsified glyceryl monostearate (HLB 4.0), glyceryl monoisostearate (HLB 4.0), glyceryl monooleate (HLB 2.5), hexaglyceryl tristearate (HLB 2.5), decaglyceryl pentastearate (HLB 3.5), decaglyceryl pentaisostearate (HLB 3.5), decaglyceryl pentaoleate (HLB 3.5), sorbitan monostearate (HLB 4.7), sorbitan tristearate (HLB 2.1), sorbitan monoisostearate (HLB 5.0), sorbitan sesquiisostearate (HLB 4.5), sorbitan monooleate (HLB 4.3), POE (6) sorbit hexastearate (HLB 3.0), POE (3) castor oil (HLB 3.0), PEG (2) monostearate (HLB 4.0), ethylene glycol monostearate (HLB 3.5), and PEG (2) stearate (HLB 4.5).

(P) Humectants

Examples of humectants include polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short-chain soluble collagen, diglycerin (EO) PO adduct, chestnut rose fruit extract, yarrow extract, and sweet clover extract.

(Q) Natural Water-Soluble Polymers

Examples of natural water-soluble polymers include: plant-type polymers (for example, gum arabic, gum tragacanth, galactan, guar gum, carob gum, karaya gum, carrageenan, pectin, agar, quince seed (*Cyclonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

(R) Semisynthetic Water-Soluble Polymers

Examples of semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymethyl cellulose, sodium carboxymethyl cellulose, crystal cellulose, and cellulose powder); and alginic acid-type polymers (for example, sodium alginate and propyleneglycol alginate).

(S) Synthetic Water-Soluble Polymers

Examples of synthetic water-soluble polymers include: vinyl polymers (for example, polyvinyl alcohol, polyvinyl methyl ether, polyvinyl pyrrolidone, and carboxy vinyl polymer); polyoxyethylene-type polymers (for example, a copolymer of polyethylene glycol 20,000, 40,000, or 60,000, and polyoxyethylene polyoxypropylene); acrylic polymers (for example, sodium polyacrylate, polyethylacrylate, and polyacrylamide); polyethyleneimine; and cationic polymers.

(T) Thickeners

Examples of thickeners include gum arabic, carrageenan, karaya gum, gum tragacanth, carob gum, quince seed (*Cyclonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, Al—Mg silicate (beagum), laponite, and silicic acid anhydride.

(U) Metal Ion Sequestering Agents

Examples of metal ion sequestering agents include 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

(V) Lower Alcohols

Examples of lower alcohols include ethanol, propanol, isopropanol, isobutyl alcohol, and t-butyl alcohol.

(W) Polyhydric Alcohols Examples of polyhydric alcohols include: dihydric alcohols (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, pentaerythritol such as 1,2,6-hexanetriol); pentahydric alcohols (for example, xylitol); hexahydric alcohols (for example, sorbitol and mannitol); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether); dihydric alcohol alkylethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin mono alkyl ethers (for example, chimyl alcohol, selachyl alcohol, and batyl alcohol); sugar alcohols (for example, sorbitol, maltitol, maltotriose, mannitol, sucrose, erythritol, glucose, fructose, starch amylolysis sugar, maltose, xylitose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether; POP-glycerin ether phosphoric acid; POP/POE-pentane erythritol ether; and polyglycerin.

(X) Monosaccharides

Examples of monosaccharides include: trioses (for example, D-glyceryl aldehyde and dihydroxyacetone); tetroses (for example, D-erythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose); deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

(Y) Oligosaccharides Examples of oligosaccharides include sucrose, umbelliferose, lactose, planteose, isolignoses, α,α-trehalose, raffinose, lignoses, umbilicine, stachyose, and verbascose.

(Z) Polysaccharides Examples of polysaccharides include cellulose, quince seed, chondroitin sulfate, starch, galactan, dermatan sulfate, glycogen, gum arabic, heparan sulfate, hyaluronic acid, traganth gum, keratan sulfate, chondroitin, xanthan gum, mucoitin sulfuric acid, guar gum, dextran, kerato sulfate, locustbean gum, succinoglucane, and charonic acid.

(AA) Amino Acids Examples of amino acids include neutral amino acids (for example, threonine and cysteine) and basic amino acids (for example, hydroxylysine).

(BB) Amino Acid Derivatives Examples of amino acid derivatives include sodium acyl sarcosinate (for example, sodium N-lauroyl sarcosinate), acyl glutamate, sodium acyl β-alanine, glutathione, and pyrrolidone carboxylic acid.

(CC) Organic Amines

Examples of organic amines include monoethanolamine, diethanolamine, triethanolamine, morpholine, triisopropanolamine, 2-amino-2-methyl-1,3-propanediol, and 2-amino-2-methyl-1-propanol.

(DD) Polymer Emulsions

Examples of polymer emulsions include acrylic resin emulsions, ethyl polyacrylate emulsions, acryl resin liquids, polyacrylic alkyl ester emulsions, polyvinyl acetate resin emulsions, and natural rubber latex.

(EE) pH Adjusting Agents

Examples of pH adjusting agents include buffers such as lactic acid-sodium lactate, citric acid-sodium citrate, and succinic acid-sodium succinate.

(FF) Vitamins

Examples of vitamins include vitamin A, B1, B2, B6, C, and E as well as their derivatives, pantothenic acid and its derivatives, and biotin.

(GG) Antioxidants

Examples of antioxidants include tocopherols, dibutyl hydroxytoluene, butyl hydroxyanisole, and gallic ester.

(HH) Antioxidation Assistants

Examples of antioxidation assistants include phosphoric acid, citric acid, ascorbic acid, maleic acid, malonic acid, succinic acid, fumaric acid, cephalin, hexametaphosphate, phytic acid, and ethylene diamine tetraacetic acid.

(II) Other Possible Ingredients

Examples of other possible ingredients include: skin nutrients; perfumes; antiseptics (for example, methylparaben, ethylparaben, butylparaben, and phenoxyethanol); anti-inflammatory agents (for example, glycyrrhizic acid derivatives, glycyrrhetinic acid derivatives, salicylic acid derivatives, hinokitiol, zinc oxide, allantoin, tranexamic acid, thiotaurine, and hypotaurine); whitening agents (for example, creeping saxifrage extract and arbutin); various extracts (for example, Phellodendri Cortex, goldthread, lithospermum root, *Paeonia lactiflora, Swertia japonica*, Birch, sage, loquat, carrot, aloe, *Malva sylvestris, Iris*, grape, *Coix ma-yuen*, sponge gourd, lily, saffron, *Cnidium officinale*, sheng jiang, *Hypericum erectum*, Ononis, garlic, Guinea pepper, chen pi, *Ligusticum acutilobum*, and seaweed); activators (for example, royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and γ-orizanol); and anti-seborrhea agents (for example, sulfur and thiantol).

(JJ) Single-Oil-Phase-Type Sunscreen Products

Optionally, a single-oil-phase-type sunscreen product of the present invention may be prepared by omitting the aqueous phase from a water-in-oil-emulsion-type sunscreen product of the present invention, that is, by not including a sufficient amount of water to form aqueous droplets within the oil phase. Such a single-oil-phase-type sunscreen product will still contain the essential ingredients of hydrophobized titanium dioxide, hydrophobized zinc oxide, and multilayer-type encapsulations containing pigments.

(2) Precursors of Water-in-Oil-Emulsion-Type Sunscreen Products

Oftentimes a user finds it more pleasant to apply a sunscreen product to the skin if the product has a lower viscosity. When the sunscreen product is of a type that is constituted by two or more phases such as of a water-in-oil-emulsion type, a decreased viscosity can facilitate macroscopic separation of the phases over time, eventually resulting, for example, in a solution in which the upper layer is the oil phase and the lower layer is the aqueous phase. This phenomenon is familiar to those having ordinary skill in the art.

For the purpose of the present invention, such a separated composition, whether originally forming a sunscreen product or resulting from just putting the ingredients together, is simply a precursor of the sunscreen product, as long as the sunscreen product can be restored or generated by stirring or agitating the separated composition for a reasonable time. In other words, a sunscreen product precursor of the present invention can be manufactured without ever forming a sunscreen product itself, and a sunscreen product precursor of the present invention might not and need not form a sunscreen product until right before it is being applied to the skin.

The sunscreen product precursor of the present invention may be provided in a container with a stirring ball or a stirring object inside, in the form of a sunscreen product package. The shape of the stirring object is not particularly limited. It may be spherical, or it may be of any other shape. The material forming the stirring object is also not particularly limited, as long as it is compatible with the sunscreen product precursor of the present invention and the container. For example, the stirring object may be made of stainless steel.

Right before use, the container may be shaken so that the movement of the ball or the object stirs or agitates the sunscreen product precursor to generate the corresponding sunscreen product. Stirring or agitating with a physical object placed inside a container may be particularly effective when the sunscreen product precursor of the present invention contains a large amount of titanium dioxide powder and zinc oxide powder. Alternatively, the container may have sufficient free space inside so that the open airspace acts as stirring objects when shaken. Or the sunscreen product precursor of the present invention may be stirred or agitated by inserting a stick or an elongated object from the outside as necessary. The inventor has discovered that the multilayer-type encapsulations containing pigments that are used in the present invention do not rupture when the container holding a sunscreen product precursor of the present invention is stirred or agitated manually to produce the corresponding sunscreen product.

(3) Multilayer-Type Encapsulations Containing Pigments

A multilayer-type encapsulation containing pigments has a structure with an inner core or layer and an outer layer or layers in which different pigments are located in the inner and outer parts. Commercially available products of multilayer-type encapsulations containing pigments include MAGICOLOR® currently sold by Biogenics, Inc., Sugarcapsule Magic SP Series currently sold by Daito Kasei Kogyo Co., Ltd., TagraCap™ currently sold by Tagra Biotechnology, and MicroBeads™ currently sold by Salvona Technologies. Multilayer-type encapsulations containing pigments may be made, for example, by: preparing a solution of first pigments, a plasticizer, and a polymer; spray-drying this solution to form core particles in which the pigments are enveloped by the polymer; dispersing these core particles in a solution containing second pigments; and spray-drying this dispersion to form encapsulated particles in which the second pigments are coated onto the polymer; such as described in United States Patent Application Publication No. US 2011/0165208 A1 (or equivalently, EP 2 474 299 A2, JP 2011-529104 A, KR 10-0978583 B1, or WO 2011/027960 A2), whose content is herein incorporated by reference in its entirety.

One of the characteristics exhibited by multilayer-type encapsulations containing pigments is sometimes referred to as "color reveal technology." Under normal conditions, the encapsulations are stable enough for the pigments to remain inside such that they do not exert the same visual, color effects as when they are exposed outside. When sufficient force is applied to the encapsulations, however, such as when a sunscreen product is manually applied to the skin, the encapsulations break up to release the pigments, thereby causing a change in the appearance of color between before and after application. The effect of encapsulation is usually to suppress largely, but not completely, a pigment's color. For example, a bulk of multilayer-type encapsulations containing red pigments appears faintly red to the eye, and a bulk of multilayer-type encapsulations containing yellow pigments appears faintly yellow to the eye.

In the present invention, the amount of multilayer-type encapsulations containing pigments that may be contained in a sunscreen product or a sunscreen product precursor is not particularly limited as long as the amount is effective in achieving desirable visual effects upon application to the skin. Preferably it is within a range between 0.1 weight % inclusive and 1.7 weight % inclusive, more preferably between 0.1 weight % inclusive and 1.6 weight % inclusive, still more preferably between 0.2 weight % inclusive and 1.2 weight % inclusive, and most preferably between 0.3 weight % inclusive and 0.9 weight % inclusive, relative to the total weight of the sunscreen product or the sunscreen product precursor. In some cases, if it is less than 0.1 weight %, the excessive whiteness that appears upon application of the sunscreen product to the skin due to titanium dioxide and zinc oxide may not be sufficiently masked. In other cases, if it is more than 1.7 weight %, the appearance of color that results upon skin application may be too thick to be natural-looking and no longer attractive to a user.

The diameter of the multilayer-type encapsulations containing pigments that are used in a sunscreen product or a sunscreen product precursor of the present invention is preferably less than 300 µm, more preferably no more than 280 µm, still more preferably no more than 250 µm, even more preferably no more than 150 µm, yet more preferably no more than 100 µm, and most preferably no more than 60 µm. Here, the diameter refers to number-average diameter. In some cases, if the diameter is 300 µm or more, a user may start to feel rough or sandy sensations when the product is applied to the skin, or there may be difficulty encountered in dispersing the encapsulations uniformly in the sunscreen product by simple stirring or agitation.

In the present invention, the color of the pigments contained in the multilayer-type encapsulations that are used in a sunscreen product or a sunscreen product precursor is not particularly limited as long as the appearance of the product is attractive to a user both before and after application to the skin. For example, for users of the Mongolian race, combinations of multilayer-type encapsulations containing red pigments and multilayer-type encapsulations containing yellow pigments can be utilized to mimic a natural-looking color of the skin, such as in a ratio of red to yellow between 1:1.8 inclusive and 1:2.2 inclusive. Combinations in different proportions and of other colors may be utilized as appropriate.

(4) Titanium Dioxide

The titanium dioxide powder ($TiO_2$) used in the present invention has been treated or processed so that its surface becomes hydrophobic ("hydrophobized titanium dioxide"). This facilitates the dispersion of titanium dioxide powder in the oil phase of a sunscreen product or a sunscreen product precursor. Examples of agents that may be used for hydrophobizing the surface of titanium dioxide include higher alcohols, hydrocarbons, triglycerides, esters, silicone oils, silicone resins, fluorine compounds, and fatty acids, such as alkyl triethoxysilane, alkyl trimethoxysilane, perfluoroalkyl phosphate, (alkyl acrylate/dimethyl silicone) copolymer, dextrin palmitate, triethoxysilylethylpolydimethylsiloxyethylhexyldimethicone, hydrogen dimethicone, dimethicone, polymeric silicone, sodium acryloyl dimethyl taurate/methacrylamide lauric acid copolymer, stearic acid, and myristic acid.

In the present invention, the amount of hydrophobized titanium dioxide contained in a sunscreen product or a sunscreen product precursor is preferably within a range between 3 weight % inclusive and 13 weight % inclusive, more preferably between 3 weight % inclusive and 11 weight % inclusive, and most preferably between 4 weight % inclusive and 9 weight % inclusive, relative to the total weight of the sunscreen product or the sunscreen product precursor. In some cases, such as non-chemical sunscreen products, if hydrophobized titanium dioxide is contained in an amount that is less than 3 weight %, sufficient ultraviolet-protection effects may not be attained. In other cases, if hydrophobized titanium dioxide is contained in an amount that is more than 13 weight %, the amount of the multilayer-type encapsulations containing pigments required to visually mask the excessive whiteness caused by titanium dioxide becomes too much and leads to degradation of the appearance of the sunscreen product upon application to the skin.

The size of the hydrophobized titanium dioxide powder that is used in a sunscreen product or a sunscreen product precursor of the present invention is not particularly limited as long as the powder exerts sufficient ultraviolet-protection effects, as commonly utilized in the art.

(5) Zinc Oxide

The zinc oxide powder (ZnO) used in the present invention has been treated or processed so that its surface becomes hydrophobic ("hydrophobized zinc oxide"). This facilitates the dispersion of zinc oxide powder in the oil phase of a sunscreen product or a sunscreen product precursor. Similarly to the case of titanium dioxide, examples of agents that may be used for hydrophobizing the surface of zinc oxide include higher alcohols, hydrocarbons, triglycerides, esters, silicone oils, silicone resins, fluorine compounds, and fatty acids, such as alkyl triethoxysilane, alkyl trimethoxysilane, perfluoroalkyl phosphate, (alkyl acrylate/dimethyl silicone) copolymer, dextrin palmitate, triethoxysilylethylpolydimethylsiloxyethylhexyldimethicone, hydrogen dimethicone, dimethicone, polymeric silicone, sodium acryloyl dimethyl taurate/methacrylamide lauric acid copolymer, stearic acid, and myristic acid.

In the present invention, the combined amount of hydrophobized titanium dioxide and hydrophobized zinc oxide contained in a sunscreen product or a sunscreen product precursor is preferably within a range between 8 weight % inclusive and 40 weight % inclusive, more preferably between 9 weight % inclusive and 40 weight % inclusive, still more preferably between 15 weight % inclusive and 35 weight % inclusive, even more preferably between 20 weight % inclusive and 30 weight % inclusive, and most preferably between 20 weight % inclusive and 27 weight % inclusive, relative to the total weight of the sunscreen product or the sunscreen product precursor. In some cases, such as non-chemical sunscreen products, if hydrophobized titanium dioxide and hydrophobized zinc oxide are contained in a combined amount that is less than 8 weight %, sufficient ultraviolet-protection effects may not be attained. In other cases, if hydrophobized titanium dioxide and hydrophobized zinc oxide are contained in a combined amount that is more than 40 weight %, the amount of the multilayer-type encapsulations containing pigments required to visually mask the excessive whiteness caused by titanium dioxide and zinc oxide becomes too much and leads to degradation of the appearance of the sunscreen product upon application to the skin.

The size of the hydrophobized zinc oxide powder that is used in a sunscreen product or a sunscreen product precursor of the present invention is not particularly limited as long as the powder exerts sufficient ultraviolet-protection effects, as commonly utilized in the art.

(6) SPF

Sun Protection Factor or Sunburn Protection Factor ("SPF") is described by the U.S. Food and Drug Administration ("FDA") as "a measure of how much solar energy (UV radiation) is required to produce sunburn on protected skin (i e, in the presence of sunscreen) relative to the amount of solar energy required to produce sunburn on unprotected skin" (from the FDA's webpage titled "About FDA—Sunburn Protection Factor (SPF)"). A higher SPF means better ultraviolet-protection effects provided by a sunscreen product.

In the present invention, an SPF exhibited by a sunscreen product is not particularly limited as long as it provides a desirable level of ultraviolet-protection effects depending on the intended use. Preferably a sunscreen product of the present invention has an SPF of 15 or more, more preferably an SPF of 20 or more, still more preferably an SPF of 30 or more, even more preferably an SPF of 40 or more, and most preferably an SPF of 50 or more. In some cases, a sunscreen product that has an SPF of less than 15 may not provide a desirable level of ultraviolet-protection effects.

(7) Viscosity

For the purpose of the present invention, viscosity is measured at 30° C. by Type-B viscometer with a rotor revolution rate of 12 per minute.

The viscosity of a sunscreen product of the present invention is not particularly limited as long as it does not hamper or interfere with its application to a user's skin and it does not affect negatively the user's sensation afterwards, and in terms of a precursor, it also does not prevent the multilayer-type encapsulations containing pigments from being uniformly dispersed and the aqueous and oil phases from forming a water-in-oil-type emulsion. Preferably the viscosity of a sunscreen product of the present invention is 10,000 mPa·s or less at 30° C., more preferably 7,000 mPa·s or less at 30° C., still more preferably 5,000 mPa·s or less at 30° C., and most preferably 3,000 mPa·s or less at 30° C. In some cases, if the viscosity of a sunscreen product exceeds 10,000 mPa·s at 30° C., a user may find the product rather unwieldy in applying it to the skin or may have a sticky feeling afterwards. Or the multilayer-type encapsulations containing pigments may not be uniformly dispersed when a precursor is stirred or agitated to form a water-in-oil-emulsion-type sunscreen product, and in addition, the aqueous and oil phases may not be sufficiently mixed to form a water-in-oil emulsion.

(8) Methods of Protecting Skin from Ultraviolet Light

In the present invention, a method of reducing skin's exposure to ultraviolet light is provided by applying a sunscreen product of the present invention to the skin. Further, in the present invention, a method of reducing skin's exposure to ultraviolet light is provided by preparing a sunscreen product of the present invention by stirring or agitating the corresponding sunscreen product precursor of the present invention, and then applying the sunscreen product to the skin.

Embodiments

Various Practice Examples of the present invention and Comparative Examples will be presented below. Table 1 lists the trade names and the INCI names of the ingredients used in those examples, which are of water-in-oil-emulsion types. (INCI stands for "International Nomenclature of Cosmetic Ingredients.") In what follows, unless otherwise specified, the amounts of the ingredients in an example composition are all expressed in weight % relative to the total amount of the composition.

In preparing the embodiments, all the oil and surfactant components were first put into a kettle and mixed by a homogenizer until the composition was uniform. Next, hydrophobized zinc oxide, hydrophobized titanium dioxide, and other powder were added one by one to the kettle, and the composition was mixed by a homogenizer until it became uniform. The water phase was then added to the kettle, and the composition was mixed by a homogenizer until it became uniform again. Finally, multilayer-type encapsulations containing pigments were added to the kettle, and the composition was mixed by gentle side sweeps.

Table 2 lists the number-average diameters or ranges of diameter of the multilayer-type encapsulations containing pigments used in the examples.

TABLE 2

| Multilayer-Type Encapsulations Containing Pigments | Number-Average Diameter or Range of Diameter |
|---|---|
| MAGICOLOR ® 103RP | 60 μm |
| MAGICOLOR ® 103YP | 60 μm |
| Sugarcapsule Magic Red SP | 70-250 μm |
| Sugarcapsule Magic Yellow SP | 70-250 μm |
| TagraCap ™ 5 Red | 70 μm |
| TagraCap ™ 5 Yellow | 70 μm |
| MicroBead ™ Red | 300 μm |
| MicroBead ™ Yellow | 300 μm |

Various properties of the examples were observed and evaluated as follows. In the Tables, "N.A." indicates that that particular property was not evaluated.

(a) Thickness of Color Before Spreading on Skin

A panel of ten experts placed a sample sunscreen product on the skin and evaluated its appearance before spreading it out on the skin.

"⊚": No expert or one expert felt discouraged from spreading out the sunscreen product on the skin due to the thickness of its color.

TABLE 1

| Component | Trade Name | INCI Name |
|---|---|---|
| Oil | Cetiol ® C5 | coco-caprylate |
| | Pripure ™ 3759 | squalane |
| | Vegelight 1214 LC | coconut alkanes, coco-caprylate/caprate |
| | Cetiol ® RLF | caprylyl caprylate/caprate, tocopherol |
| Surfactant | Wogel 18DV | polyglyceryl-2 diisostearate |
| | Estemol 182V | sorbitan sesquiisostearate |
| | Isostearic Acid SX | isostearic acid |
| Hydrophobized Zinc Oxide | OTS-ZNO-660USP | zinc oxide, triethoxycaprylylsilane |
| | MT-FINEX25 | zinc oxide, myristic acid |
| Hydrophobized Titanium Dioxide | OTQ-MT 100SI | titanium dioxide, hydrated silica, triethoxycaprylylsilane, distearyldimonium chloride |
| | A2289-24 | titanium dioxide 82.6%, magnesium isostearate 17.4% |
| | MT-100EMG (lot. T45-01) | titanium dioxide 82.6%, magnesium isostearate 17.4% |
| Powder | Sunsphere L-51S | silica |
| | Penstia ™ Powder | adipic acid/neopentyl glycol crosspolymer |
| Multilayer-Type Encapsulations Containing Pigments | MAGICOLOR ® 103RP | titanium dioxide, iron oxide, mica, silica dimethyl silylate, polyester-1 |
| | MAGICOLOR ® 103YP | titanium dioxide, iron oxide, mica, silica dimethyl silylate, polyester-1 |
| | Sugarcapsule Magic Red SP | mannitol, iron oxide, hydrogenated lecithin, titanium dioxide, aluminum hydroxide, polymethyl methacrylate |
| | Sugarcapsule Magic Yellow SP | mannitol, iron oxide, hydrogenated lecithin, titanium dioxide, aluminum hydroxide, polymethyl methacrylate |
| | TagraCap ™ 5 Red | iron oxide, titanium dioxide, boron nitride, acrylate/ammonium methacrylate copolymer |
| | TagraCap ™ 5 Yellow | iron oxide, titanium dioxide, boron nitride, acrylate/ammonium methacrylate copolymer |
| | MicroBead ™ Red | titanium dioxide, sucrose, iron oxide red, mica, ethyl cellulose, hydroxypropyl methyl cellulose |
| | MicroBead ™ Yellow | titanium dioxide, sucrose, iron oxide yellow, mica, ethyl cellulose, hydroxypropyl methyl cellulose |
| Water | Deionized Water | water |

"○": Between two and four experts felt discouraged from spreading out the sunscreen product on the skin due to the thickness of its color.

"x": Five or more experts felt discouraged from spreading out the sunscreen product on the skin due to the thickness of its color.

(b) Thickness of Color while Spreading on Skin

A panel of ten experts placed a sample sunscreen product on the skin and evaluated its appearance while spreading it out on the skin.

"◉": No expert or one expert felt discouraged from continuing to spread out the sunscreen product on the skin due to the thickness of its color.

"○": Between two and four experts felt discouraged from continuing to spread out the sunscreen product on the skin due to the thickness of its color.

"x": Five or more experts felt discouraged from continuing to spread out the sunscreen product on the skin due to the thickness of its color.

(c) Effects of Stirring on Macroscopic Mixing

Components of a sample sunscreen product and a stirring ball were placed in a container, and the container was closed and shaken vertically for twenty cycles. The sample was then observed to evaluate whether it was mixed uniformly on a macroscopic scale to form a water-in-oil emulsion.

"◉": The sample was mixed uniformly on a macroscopic scale to form a water-in-oil emulsion.

"x": The sample was not mixed uniformly on a macroscopic scale, and a water-in-oil emulsion was not formed.

(d) Effects of Stirring on Dispersion of Encapsulations

Components of a sample sunscreen product and a stirring ball were placed in a container, and the container was closed and shaken vertically for twenty cycles. The sample was then observed through a microscope to evaluate whether the multilayer-type encapsulations containing pigments were dispersed uniformly.

"◉": The encapsulations were dispersed uniformly in the oil phase.

"○": The encapsulations were dispersed almost uniformly in the oil phase.

"x": Precipitates were observed, and the encapsulations were not dispersed uniformly.

(e) Extent of Masking Excessive Whiteness Upon Application to Skin

A panel of ten experts applied a sample sunscreen product to the skin and evaluated any excessive whiteness that appeared.

"◉": Nine or ten experts observed no excessive whiteness.

"○": Between six and eight experts observed no excessive whiteness.

"x": Five or less experts observed no excessive whiteness.

(f) Appearance of Color Upon Application to Skin

A panel of ten experts applied a sample sunscreen product to the skin and evaluated how natural-looking the color that resulted was.

"◉": Nine or ten experts judged the color to be natural-looking

"○": Between six and eight experts judged the color to be natural-looking

"x": Five or less experts judged the color to be natural-looking (g) Physical Sensation Upon Application to Skin A panel of ten experts applied a sample sunscreen product to the skin and evaluated whether a rough or sandy sensation arose.

"◉": Nine or ten experts felt no rough or sandy sensation.

"○": Between six and eight experts felt no rough or sandy sensation.

"x": Five or less experts felt no rough or sandy sensation.

(1) Effects of Amounts of Titanium Dioxide and Zinc Oxide

Table 3 shows the compositions of Comparative Examples 1 and 2, as well as some of the properties observed for each. The compositions contain no pigments, and differ in the amounts of hydrophobized titanium dioxide and hydrophobized zinc oxide that were added. The difference in weight was made up for by adjusting the amount of the oil component (Vegelight 1214 LC).

The results indicate that with no pigments, excessive whiteness did not appear when the total amount of hydrophobized titanium dioxide and hydrophobized zinc oxide was 4 weight % (Comparative Example 1), but excessive whiteness appeared when the total amount of hydrophobized titanium dioxide and hydrophobized zinc oxide was 9 weight % (Comparative Example 2).

TABLE 3

| Component | Trade Name | Comparative Example 1 | Comparative Example 2 |
|---|---|---|---|
| Oil | Cetiol ® C5 | 5 | 5 |
| | Pripure ™ 3759 | 5 | 5 |
| | Vegelight 1214 LC | 53.6 | 48.6 |
| | Cetiol ® RLF | 5 | 5 |
| Surfactant | Wogel 18DV | 2 | 2 |
| | Estemol 182V | 2 | 2 |
| | Isostearic Acid SX | 2 | 2 |
| Hydrophobized Zinc Oxide | MT-FINEX25 | 1 | 5 |
| Hydrophobized Titanium Dioxide | MT-100EMG (lot. T45-01) | 3 | 4 |
| Powder | Sunsphere L-51S | 5.4 | 5.4 |
| | Penstia ™ Powder | 1 | 1 |
| Water | Deionized water | 15 | 15 |
| | Total | 100 | 100 |
| Properties | Viscosity (mPa · s) | 40 | 600 |
| | (c) Mixing | ◉ | ◉ |
| | (e) Whiteness | ◉ | X |

(2) Comparison of Effects of Naked Pigments and of Encapsulations Containing Pigments Table 4 shows the compositions of Comparative Example 3 and Practice Example 2, as well as some of the properties observed for each. Comparative Example 3 contains naked pigments (i.e., Unipure Red LC 381 LL and Unipure Yellow LC 182 LL), and Practice Example 2 contains multilayer-type encapsulations containing pigments (i.e., MAGICOLOR® 103RP and MAGICOLOR® 103YP). The amount of the naked pigments in Comparative Example 3 was chosen so that it would contain the same amount of raw pigments as in Practice Example 2 based on the fact that the iron oxide content in MAGICOLOR® is 48 weight %. The difference in weight was made up for by adjusting the amount of the oil component (Vegelight 1214 LC).

The results indicate that when naked pigments were used as in Comparative Example 3, the color thickness of the sunscreen product both in bulk and on the skin was not desirable. Comparative Example 3 in these states is shown in FIGS. 2A and 2B, respectively. On the other hand, when multilayer-type encapsulations containing pigments were used as in Practice Example 2, the color thickness of the sunscreen product both in bulk and on the skin was good.

TABLE 4

| Component | Trade Name | Comparative Example 3 | Practice Example 2 |
|---|---|---|---|
| Oil | Cetiol® C5 | 5 | 5 |
|  | Pripure™ 3759 | 5 | 5 |
|  | Vegelight 1214 LC | 27.456 | 27.3 |
|  | Cetiol® RLF | 5 | 5 |
| Surfactant | Wogel 18DV | 2 | 2 |
|  | Estemol 182V | 2 | 2 |
|  | Isostearic Acid SX | 2 | 2 |
| Hydrophobized Zinc Oxide | MT-FINEX25 | 25 | 25 |
| Hydrophobized Titanium Dioxide | MT-100EMG (lot. T45-01) | 5 | 5 |
| Powder | Sunsphere L-51S | 5.4 | 5.4 |
|  | Penstia™ Powder | 1 | 1 |
| Multilayer-Type Encapsulations Containing Pigments | MAGICOLOR® 103RP | — | 0.1 |
|  | MAGICOLOR® 103YP | — | 0.2 |
| Naked Pigments | Unipure Red LC 381 LL (iron oxides, lauroyl lysine) | 0.048 | — |
|  | Unipure Yellow LC 182 LL (iron oxides, lauroyl lysine) | 0.096 | — |
| Water | Deionized water | 15 | 15 |
|  | Total | 100 | 100 |
| Properties | Viscosity (mPa · s) | 3000 | 2000 |
|  | (a) Color thickness before spreading | X | ◎ |
|  | (b) Color thickness while spreading | X | ◎ |
|  | (c) Mixing | ◎ | ◎ |
|  | (e) Whiteness | N.A. | ◎ |

(3) Effects of Amount of Encapsulations Containing Pigments

Table 5 shows the compositions of Comparative Examples 4 and 5 and Practice Examples 1-5, as well as some of the properties observed for each. The compositions differ in the amount of the multilayer-type encapsulations containing pigments that were added, and the differences in weight were made up for by adjusting the amount of the oil component (Vegelight 1214 LC).

The results indicate that the excessive whiteness arising from hydrophobized titanium dioxide and hydrophobized zinc oxide upon applying the sunscreen product to the skin was not sufficiently masked when the amount of the encapsulations used was less than approximately 0.1 weight % (i.e., between Comparative Example 4 and Practice Example 1). FIGS. 1A and 1B show Comparative Example 4 before and after it is spread out on the skin, respectively. On the other hand, when the amount of the encapsulations used was more than approximately 1.7 weight %, the appearance of color on the skin was no longer natural-looking (i.e., between Practice Example 5 and Comparative Example 5). FIGS. 3A and 3B show Practice Example 3 before and after it is spread out on the skin, respectively.

TABLE 5

| Component | Trade Name | Comparative Example 4 | Practice Example 1 | Practice Example 2 | Practice Example 3 | Practice Example 4 | Practice Example 5 | Comparative Example 5 |
|---|---|---|---|---|---|---|---|---|
| Oil | Cetiol® C5 | 5 | 5 | 5 | 5 | 5 | 5 | 5 |
|  | Pripure™ 3759 | 5 | 5 | 5 | 5 | 5 | 5 | 5 |
|  | Vegelight 1214 LC | 27.6 | 27.45 | 27.3 | 27 | 26.7 | 26.1 | 25.8 |
|  | Cetiol® RLF | 5 | 5 | 5 | 5 | 5 | 5 | 5 |
| Surfactant | Wogel 18DV | 2 | 2 | 2 | 2 | 2 | 2 | 2 |
|  | Estemol 182V | 2 | 2 | 2 | 2 | 2 | 2 | 2 |
|  | Isostearic Acid SX | 2 | 2 | 2 | 2 | 2 | 2 | 2 |
| Hydrophobized ZnO | MT-FINEX25 | 25 | 25 | 25 | 25 | 25 | 25 | 25 |
| Hydrophobized TiO$_2$ | MT-100EMG (lot. T45-01) | 5 | 5 | 5 | 5 | 5 | 5 | 5 |
| Powder | Sunsphere L-51S | 5.4 | 5.4 | 5.4 | 5.4 | 5.4 | 5.4 | 5.4 |
|  | Penstia™ Powder | 1 | 1 | 1 | 1 | 1 | 1 | 1 |
| Encapsulations | MAGICOLOR® 103RP | — | 0.05 | 0.1 | 0.2 | 0.3 | 0.5 | 0.6 |
|  | MAGICOLOR® 103YP | — | 0.1 | 0.2 | 0.4 | 0.6 | 1 | 1.2 |
| Water | Deionized water | 15 | 15 | 15 | 15 | 15 | 15 | 15 |
|  | Total | 100 | 100 | 100 | 100 | 100 | 100 | 100 |
| Properties | Viscosity (mPa · s) | 2200 | 2320 | 2000 | 2180 | 2320 | 2210 | 2130 |
|  | (c) Mixing | ◎ | ◎ | ◎ | ◎ | ◎ | ◎ | ◎ |
|  | (d) Dispersion | N.A. | N.A. | N.A. | ◎ | ◎ | ◎ | ◎ |
|  | (e) Whiteness | X | ○ | ◎ | ◎ | ◎ | ◎ | ◎ |
|  | (f) Naturalness | N.A. | N.A. | N.A. | ◎ | ◎ | ◎ | X |
|  | (g) Sensation | N.A. | N.A. | N.A. | ◎ | ◎ | ◎ | ◎ |

(4) Effects of Size of Encapsulations

Table 6 shows the compositions of Practice Examples 3, 6, and 7 and Comparative Example 6, as well as some of the properties observed for each. The examples differ only in the size of the multilayer-type encapsulations containing pigments that were used as expressed by number-average diameter or range of diameter.

The results indicate that the properties of the sunscreen product and its precursor started to deteriorate when the diameter of the encapsulations became 300 μm. Specifically, as shown by Comparative Example 6, when the diameter of the encapsulations was 300 μm, the encapsulations did not disperse well upon stirring the sunscreen product precursor, the excessive whiteness due to hydrophobized titanium dioxide and hydrophobized zinc oxide was not sufficiently masked upon application of the sunscreen product to the skin, and the sensation on the skin was not good.

pigments was increased as necessary so that the excessive whiteness arising from the hydrophobized titanium dioxide and the hydrophobized zinc oxide was sufficiently masked, but this amount was capped at 1.5 weight % since Table 5 above shows that the appearance of color on the skin was natural-looking in Practice Example 5 (which contained 1.5 weight % of the encapsulations) but was not natural-looking in Comparative Example 5 (which contained 1.8 weight % of the encapsulations). The differences in weight were made up for by adjusting the amounts of the oil component (Vegelight 1214 LC) and the powder component (Sunsphere L-51S and Penstia™ Powder).

The results indicate that when the viscosity became more than approximately 10,000 mPa·s due to the increased amount of hydrophobized titanium dioxide and hydrophobized zinc oxide, the properties of the sunscreen product and its precursor started to deteriorate. Specifically, as shown by

TABLE 6

| Component | Trade Name | Practice Example 3 | Practice Example 6 | Practice Example 7 | Comparative Example 6 |
|---|---|---|---|---|---|
| Oil | Cetiol ® C5 | 5 | 5 | 5 | 5 |
| | Pripure ™ 3759 | 5 | 5 | 5 | 5 |
| | Vegelight 1214 LC | 27 | 27 | 27 | 27 |
| | Cetiol ® RLF | 5 | 5 | 5 | 5 |
| Surfactant | Wogel 18DV | 2 | 2 | 2 | 2 |
| | Estemol 182V | 2 | 2 | 2 | 2 |
| | Isostearic Acid SX | 2 | 2 | 2 | 2 |
| Hydrophobized Zinc Oxide | MT-FINEX25 | 25 | 25 | 25 | 25 |
| Hydrophobized Titanium Dioxide | MT-100EMG (lot. T45-01) | 5 | 5 | 5 | 5 |
| Powder | Sunsphere L-51S | 5.4 | 5.4 | 5.4 | 5.4 |
| | Penstia ™ Powder | 1 | 1 | 1 | 1 |
| Multilayer-Type Encapsulations Containing Pigments | MAGICOLOR ® 103RP | 0.2 | — | — | — |
| | MAGICOLOR ® 103YP | 0.4 | — | — | — |
| | Sugarcapsule Magic Red SP | — | 0.2 | — | — |
| | Sugarcapsule Magic Yellow SP | — | 0.4 | — | — |
| | TagraCap ™ 5 Red | — | — | 0.2 | — |
| | TagraCap ™ 5 Yellow | — | — | 0.4 | — |
| | MicroBead ™ Red | — | — | — | 0.2 |
| | MicroBead ™ Yellow | — | — | — | 0.4 |
| Water | Deionized water | 15 | 15 | 15 | 15 |
| | Total | 100 | 100 | 100 | 100 |
| Properties | Viscosity (mPa·s) | 2180 | 2220 | 2350 | 2100 |
| | (c) Mixing | ⊚ | ⊚ | ⊚ | ⊚ |
| | (d) Dispersion | ⊚ | ⊚ | ⊚ | X |
| | (e) Whiteness | ⊚ | ⊚ | ⊚ | X |
| | (g) Sensation | ⊚ | ⊚ | ⊚ | X |

(5) Effects of Combined Amount of Hydrophobized Titanium Dioxide and Hydrophobized Zinc Oxide and of Viscosity Table 7 shows the compositions of Comparative Example 7 and Practice Examples 3 and 8-12, as well as some of the properties observed for each. The compositions differ in the combined amount of hydrophobized titanium dioxide and hydrophobized zinc oxide that were added. At the same time, the amount of the multilayer-type encapsulations containing Practice Example 12 and Comparative Example 7, the aqueous and oil phases did not mix well to form a water-in-oil emulsion, and the encapsulations did not disperse well, upon stirring the sunscreen product precursor, and the excessive whiteness arising from hydrophobized titanium dioxide and hydrophobized zinc oxide was not sufficiently masked upon application of the sunscreen product to the skin while maintaining natural-looking color.

TABLE 7

| Component | Trade Name | Practice Example 8 | Practice Example 9 | Practice Example 3 | Practice Example 10 | Practice Example 11 | Practice Example 12 | Comparative Example 7 |
|---|---|---|---|---|---|---|---|---|
| Oil | Cetiol ® C5 | 5 | 5 | 5 | 5 | 5 | 5 | 5 |
| | Pripure ™ 3759 | 5 | 5 | 5 | 5 | 5 | 5 | 5 |
| | Vegelight 1214 LC | 40 | 37 | 27 | 26 | 23.4 | 25.5 | 22.5 |
| | Cetiol ® RLF | 5 | 5 | 5 | 5 | 5 | 5 | 5 |
| Surfactant | Wogel 18DV | 2 | 2 | 2 | 2 | 2 | 2 | 2 |
| | Estemol 182V | 2 | 2 | 2 | 2 | 2 | 2 | 2 |
| | Isostearic Acid SX | 2 | 2 | 2 | 2 | 2 | 2 | 2 |
| Hydrophobized ZnO | MT-FINEX25 | 13 | 16 | 25 | 25 | 25 | 25 | 25 |
| Hydrophobized TiO$_2$ | MT-100EMG (lot. T45-01) | 4 | 4 | 5 | 7 | 10 | 12 | 15 |
| Powder | Sunsphere L-51S | 5.4 | 5.4 | 5.4 | 4.4 | 3.4 | — | — |
| | Penstia ™ Powder | 1 | 1 | 1 | 1 | 1 | — | — |
| Encapsulations | MAGICOLOR ® 103RP | 0.2 | 0.2 | 0.2 | 0.2 | 0.4 | 0.5 | 0.5 |
| | MAGICOLOR ® 103YP | 0.4 | 0.4 | 0.4 | 0.4 | 0.8 | 1 | 1 |
| Water | Deionized water | 15 | 15 | 15 | 15 | 15 | 15 | 15 |
| | Total | 100 | 100 | 100 | 100 | 100 | 100 | 100 |
| Properties | Viscosity (mPa·s) | 500 | 1820 | 2180 | 4300 | 7700 | 9000 | 15000 |
| | (c) Mixing | ◎ | ◎ | ◎ | ◎ | ◎ | ◎ | X |
| | (d) Dispersion | ◎ | ◎ | ◎ | ◎ | ◎ | ○ | X |
| | (e) Whiteness | ◎ | ◎ | ◎ | ◎ | ◎ | ○ | X |

(6) Effects of Viscosity

Table 8 shows the compositions of Practice Examples 3 and 13-15 and Comparative Example 8, as well as some of the properties observed for each. The compositions differ only in the types of hydrophobized titanium dioxide and zinc oxide used, not in the amounts added. Most importantly, the zinc oxide used in Comparative Example 8 was not hydrophobized. The differences in the types of inorganic, ultraviolet-scattering components result in varying viscosities of the sunscreen products produced, in particular in a sharp rise in viscosity when zinc oxide is not hydrophobized as seen in Comparative Example 8.

The results indicate that the properties of the sunscreen product precursor were not desirable when the viscosity was 16,000 mPa·s as shown by Comparative Example 8. Specifically, the aqueous and oil phases did not mix well to form a water-in-oil emulsion, and the multilayer-type encapsulations containing pigments did not disperse well, upon stirring the sunscreen product precursor.

TABLE 8

| Component | Trade Name | Practice Example 3 | Practice Example 13 | Practice Example 14 | Practice Example 15 | Comparative Example 8 |
|---|---|---|---|---|---|---|
| Oil | Cetiol ® C5 | 5 | 5 | 5 | 5 | 5 |
| | Pripure ™ 3759 | 5 | 5 | 5 | 5 | 5 |
| | Vegelight 1214 LC | 27 | 27 | 27 | 27 | 27 |
| | Cetiol ® RLF | 5 | 5 | 5 | 5 | 5 |
| Surfactant | Wogel 18DV | 2 | 2 | 2 | 2 | 2 |
| | Estemol 182V | 2 | 2 | 2 | 2 | 2 |
| | Isostearic Acid SX | 2 | 2 | 2 | 2 | 2 |
| Hydrophobized Zinc Oxide | OTS-ZNO-660USP | — | 25 | — | — | — |
| | MT-FINEX25 | 25 | — | 25 | 25 | — |
| Zinc Oxide | FINEX30W (zinc oxide (72-78%), hydrated silica (17-23%)) | — | — | — | — | 25 |
| Hydrophobized Titanium Dioxide | OTQ-MT 100SI A2289-24 | — | — | — | 5 | — |
| | MT-100EMG (lot. T45-01) | 5 | 5 | — | — | 5 |
| Powder | Sunsphere L-51S | 5.4 | 5.4 | 5.4 | 5.4 | 5.4 |
| | Penstia ™ Powder | 1 | 1 | 1 | 1 | 1 |
| Encapsulations | MAGICOLOR ® 103RP | 0.2 | 0.2 | 0.2 | 0.2 | 0.2 |
| | MAGICOLOR ® 103YP | 0.4 | 0.4 | 0.4 | 0.4 | 0.4 |
| Water | Deionized water | 15 | 15 | 15 | 15 | 15 |
| | Total | 100 | 100 | 100 | 100 | 100 |

TABLE 8-continued

| Component | Trade Name | Practice Example 3 | Practice Example 13 | Practice Example 14 | Practice Example 15 | Comparative Example 8 |
|---|---|---|---|---|---|---|
| Properties | Viscosity (mPa · s) | 2180 | 2300 | 2000 | 2200 | 16000 |
| | (c) Mixing | ⊚ | ⊚ | ⊚ | ⊚ | X |
| | (d) Dispersion | ⊚ | ⊚ | ⊚ | ⊚ | X |
| | (e) Whiteness | ⊚ | ⊚ | ⊚ | ⊚ | ⊚ |
| | (f) Naturalness | ⊚ | ⊚ | ⊚ | ⊚ | ⊚ |
| | (g) Sensation | ⊚ | ⊚ | ⊚ | ⊚ | ⊚ |

Now that exemplary embodiments of the present invention have been shown and described in detail, various modifications and improvements thereon will become readily apparent to those skilled in the art.

It will be understood that one or more of the elements or exemplary embodiments described can be rearranged, separated, or combined without deviating from the scope of the present invention. For ease of description, various elements are, at times, presented separately. This is merely for convenience and is in no way meant to be a limitation.

Further, it will be understood that one or more of the steps described can be rearranged, separated, or combined without deviating from the scope of the present invention. For ease of description, steps are, at times, presented sequentially. This is merely for convenience and is in no way meant to be a limitation.

While the various elements, steps, and exemplary embodiments of the present invention have been outlined above, it is evident that many alternatives, modifications, and variations will be apparent to those skilled in the art. The various elements, steps, and exemplary embodiments of the present invention, as described above, are intended to be illustrative, not limiting. Various changes can be made without departing from the spirit and scope of the present disclosure. Accordingly, the spirit and scope of the present disclosure is to be construed broadly and not limited by the foregoing specification.

No element, act, or instruction used in the description of the present invention should be construed as critical or essential unless explicitly described as such. Also, as used herein, the article "a" is intended to include one or more items. Where only one item is intended, the term "one," "single," or similar language is used.

The present invention has industrial applicability in that it provides, among other things, a sunscreen product useful in protecting the skin from ultraviolet light, a precursor useful in preparing such a sunscreen product, and a method of preparing the sunscreen product from its precursor.

What is claimed is:

1. A water-in-oil-emulsion-type sunscreen product, comprising:
   hydrophobized titanium dioxide;
   hydrophobized zinc oxide; and
   multilayer-type encapsulations containing pigments and the pigments are not hydrophobized titanium dioxide or hydrophobized zinc oxide;
   wherein:
   the amount of the hydrophobized titanium dioxide is between 3 weight % inclusive and 13 weight % inclusive;
   the combined amount of the hydrophobized titanium dioxide and the hydrophobized zinc oxide is between 8 weight % inclusive and 40 weight % inclusive; the weight % is relative to the total amount of the water-in-oil-emulsion-type sunscreen product;
   the multilayer-type encapsulations containing pigments have a number-average diameter of less than 300 μm; and
   the viscosity of the water-in-oil-emulsion-type sunscreen product is 10,000 mPa·s or less at 30° C. as measured by Type-B viscometer with a rotor revolution rate of 12 per minute.

2. The water-in-oil-emulsion-type sunscreen product according to claim 1, wherein the amount of the multilayer-type encapsulations containing pigments is between 0.1 weight % inclusive and 1.7 weight % inclusive.

3. The water-in-oil-emulsion-type sunscreen product according to claim 2, wherein the amount of the multilayer-type encapsulations containing pigments is between 0.1 weight % inclusive and 1.6 weight % inclusive.

4. The water-in-oil-emulsion-type sunscreen product according to claim 3, wherein the amount of the multilayer-type encapsulations containing pigments is between 0.2 weight % inclusive and 1.2 weight % inclusive.

5. The water-in-oil-emulsion-type sunscreen product according to claim 4, wherein the amount of the multilayer-type encapsulations containing pigments is between 0.3 weight % inclusive and 0.9 weight % inclusive.

6. The water-in-oil-emulsion-type sunscreen product according to claim 1, wherein the number-average diameter of the multilayer-type encapsulations containing pigments is 280 μm or less.

7. The water-in-oil-emulsion-type sunscreen product according to claim 6, wherein the number-average diameter of the multilayer-type encapsulations containing pigments is 250 μm or less.

8. The water-in-oil-emulsion-type sunscreen product according to claim 7, wherein the number-average diameter of the multilayer-type encapsulations containing pigments is 150 μm or less.

9. The water-in-oil-emulsion-type sunscreen product according to claim 8, wherein the number-average diameter of the multilayer-type encapsulations containing pigments is 100 μm or less.

10. The water-in-oil-emulsion-type sunscreen product according to claim 9, wherein the number-average diameter of the multilayer-type encapsulations containing pigments is 60 μm or less.

11. The water-in-oil-emulsion-type sunscreen product according to claim 7, wherein the amount of the multilayer-type encapsulations containing pigments is between 0.2 weight % inclusive and 1.2 weight % inclusive.

12. The water-in-oil-emulsion-type sunscreen product according to claim 11, wherein the amount of the multilayer-type encapsulations containing pigments is between 0.3 weight % inclusive and 0.9 weight % inclusive.

13. The water-in-oil-emulsion-type sunscreen product according to claim 12, wherein the amount of the hydrophobized titanium dioxide is between 4 weight % inclusive and 9 weight % inclusive.

14. The water-in-oil-emulsion-type sunscreen product according to claim 10, wherein the amount of the multilayer-type encapsulations containing pigments is between 0.2 weight % inclusive and 1.2 weight % inclusive.

15. The water-in-oil-emulsion-type sunscreen product according to claim 14, wherein the amount of the multilayer-type encapsulations containing pigments is between 0.3 weight % inclusive and 0.9 weight % inclusive.

16. The water-in-oil-emulsion-type sunscreen product according to claim 15, wherein the amount of the hydrophobized titanium dioxide is between 4 weight % inclusive and 9 weight % inclusive.

17. A method of reducing exposure of human skin to ultraviolet light, comprising the step of applying the water-in-oil-emulsion-type sunscreen product according to claim 1 to the human skin.

18. A method of reducing exposure of human skin to ultraviolet light, comprising the step of applying the water-in-oil-emulsion-type sunscreen product according to claim 2 to the human skin.

19. A method of reducing exposure of human skin to ultraviolet light, comprising the step of applying the water-in-oil-emulsion-type sunscreen product according to claim 3 to the human skin.

20. A method of reducing exposure of human skin to ultraviolet light, comprising the step of applying the water-in-oil-emulsion-type sunscreen product according to claim 4 to the human skin.

21. A method of reducing exposure of human skin to ultraviolet light, comprising the step of applying the water-in-oil-emulsion-type sunscreen product according to claim 5 to the human skin.

22. A method of reducing exposure of human skin to ultraviolet light, comprising the step of applying the water-in-oil-emulsion-type sunscreen product according to claim 6 to the human skin.

23. A method of reducing exposure of human skin to ultraviolet light, comprising the step of applying the water-in-oil-emulsion-type sunscreen product according to claim 7 to the human skin.

24. A method of reducing exposure of human skin to ultraviolet light, comprising the step of applying the water-in-oil-emulsion-type sunscreen product according to claim 8 to the human skin.

25. A method of reducing exposure of human skin to ultraviolet light, comprising the step of applying the water-in-oil-emulsion-type sunscreen product according to claim 9 to the human skin.

26. A method of reducing exposure of human skin to ultraviolet light, comprising the step of applying the water-in-oil-emulsion-type sunscreen product according to claim 10 to the human skin.

27. A method of reducing exposure of human skin to ultraviolet light, comprising the step of applying the water-in-oil-emulsion-type sunscreen product according to claim 11 to the human skin.

28. A method of reducing exposure of human skin to ultraviolet light, comprising the step of applying the water-in-oil-emulsion-type sunscreen product according to claim 12 to the human skin.

29. A method of reducing exposure of human skin to ultraviolet light, comprising the step of applying the water-in-oil-emulsion-type sunscreen product according to claim 13 to the human skin.

30. A method of reducing exposure of human skin to ultraviolet light, comprising the step of applying the water-in-oil-emulsion-type sunscreen product according to claim 14 to the human skin.

31. A method of reducing exposure of human skin to ultraviolet light, comprising the step of applying the water-in-oil-emulsion-type sunscreen product according to claim 15 to the human skin.

32. A method of reducing exposure of human skin to ultraviolet light, comprising the step of applying the water-in-oil-emulsion-type sunscreen product according to claim 16 to the human skin.

33. A sunscreen product precursor, comprising:
an oil-phase solvent;
hydrophobized titanium dioxide;
hydrophobized zinc oxide;
multilayer-type encapsulations containing pigments; and
water;
wherein:
the amount of the hydrophobized titanium dioxide is between 3 weight % inclusive and 13 weight % inclusive;
the combined amount of the hydrophobized titanium dioxide and the hydrophobized zinc oxide is between 8 weight % inclusive and 40 weight % inclusive;
the amount of water is between 0.01 weight % inclusive and 98 weight % inclusive;
the weight % is relative to the total amount of the sunscreen product precursor; and
the multilayer-type encapsulations containing pigments have a number-average diameter of less than 300 μm.

34. The sunscreen product precursor according to claim 33, wherein the amount of the multilayer-type encapsulations containing pigments is between 0.1 weight % inclusive and 1.7 weight % inclusive.

35. The sunscreen product precursor according to claim 34, wherein the amount of the multilayer-type encapsulations containing pigments is between 0.1 weight % inclusive and 1.6 weight % inclusive.

36. The sunscreen product precursor according to claim 35, wherein the amount of the multilayer-type encapsulations containing pigments is between 0.2 weight % inclusive and 1.2 weight % inclusive.

37. The sunscreen product precursor according to claim 36, wherein the amount of the multilayer-type encapsulations containing pigments is between 0.3 weight % inclusive and 0.9 weight % inclusive.

38. The sunscreen product precursor according to claim 33, wherein the number-average diameter of the multilayer-type encapsulations containing pigments is 280 μm or less.

39. The sunscreen product precursor according to claim 38, wherein the number-average diameter of the multilayer-type encapsulations containing pigments is 250 μm or less.

40. The sunscreen product precursor according to claim 39, wherein the number-average diameter of the multilayer-type encapsulations containing pigments is 150 μm or less.

41. The sunscreen product precursor according to claim 40, wherein the number-average diameter of the multilayer-type encapsulations containing pigments is 100 μm or less.

42. The sunscreen product precursor according to claim 41, wherein the number-average diameter of the multilayer-type encapsulations containing pigments is 60 μm or less.

43. The sunscreen product precursor according to claim 39, wherein the amount of the multilayer-type encapsulations containing pigments is between 0.2 weight % inclusive and 1.2 weight % inclusive.

44. The sunscreen product precursor according to claim 43, wherein the amount of the multilayer-type encapsulations containing pigments is between 0.3 weight % inclusive and 0.9 weight % inclusive.

45. The sunscreen product precursor according to claim 44, wherein the amount of the hydrophobized titanium dioxide is between 4 weight % inclusive and 9 weight % inclusive.

46. The sunscreen product precursor according to claim 42, wherein the amount of the multilayer-type encapsulations containing pigments is between 0.2 weight % inclusive and 1.2 weight % inclusive.

47. The sunscreen product precursor according to claim 46, wherein the amount of the multilayer-type encapsulations containing pigments is between 0.3 weight % inclusive and 0.9 weight % inclusive.

48. The sunscreen product precursor according to claim 47, wherein the amount of the hydrophobized titanium dioxide is between 4 weight % inclusive and 9 weight % inclusive.

49. A method of reducing exposure of human skin to ultraviolet light, comprising the steps of:
preparing a water-in-oil-emulsion-type sunscreen product by stirring or agitating the sunscreen product precursor according to claim 33; and
applying the water-in-oil-emulsion-type sunscreen product to the human skin.

50. A method of reducing exposure of human skin to ultraviolet light, comprising the steps of:
preparing a water-in-oil-emulsion-type sunscreen product by stirring or agitating the sunscreen product precursor according to claim 34; and
applying the water-in-oil-emulsion-type sunscreen product to the human skin.

51. A method of reducing exposure of human skin to ultraviolet light, comprising the steps of:
preparing a water-in-oil-emulsion-type sunscreen product by stirring or agitating the sunscreen product precursor according to claim 35; and
applying the water-in-oil-emulsion-type sunscreen product to the human skin.

52. A method of reducing exposure of human skin to ultraviolet light, comprising the steps of:
preparing a water-in-oil-emulsion-type sunscreen product by stirring or agitating the sunscreen product precursor according to claim 36; and
applying the water-in-oil-emulsion-type sunscreen product to the human skin.

53. A method of reducing exposure of human skin to ultraviolet light, comprising the steps of:
preparing a water-in-oil-emulsion-type sunscreen product by stirring or agitating the sunscreen product precursor according to claim 37; and
applying the water-in-oil-emulsion-type sunscreen product to the human skin.

54. A method of reducing exposure of human skin to ultraviolet light, comprising the steps of:
preparing a water-in-oil-emulsion-type sunscreen product by stirring or agitating the sunscreen product precursor according to claim 38; and
applying the water-in-oil-emulsion-type sunscreen product to the human skin.

55. A method of reducing exposure of human skin to ultraviolet light, comprising the steps of:
preparing a water-in-oil-emulsion-type sunscreen product by stirring or agitating the sunscreen product precursor according to claim 39; and
applying the water-in-oil-emulsion-type sunscreen product to the human skin.

56. A method of reducing exposure of human skin to ultraviolet light, comprising the steps of:
preparing a water-in-oil-emulsion-type sunscreen product by stirring or agitating the sunscreen product precursor according to claim 40; and
applying the water-in-oil-emulsion-type sunscreen product to the human skin.

57. A method of reducing exposure of human skin to ultraviolet light, comprising the steps of:
preparing a water-in-oil-emulsion-type sunscreen product by stirring or agitating the sunscreen product precursor according to claim 41; and
applying the water-in-oil-emulsion-type sunscreen product to the human skin.

58. A method of reducing exposure of human skin to ultraviolet light, comprising the steps of:
preparing a water-in-oil-emulsion-type sunscreen product by stirring or agitating the sunscreen product precursor according to claim 42; and
applying the water-in-oil-emulsion-type sunscreen product to the human skin.

59. A method of reducing exposure of human skin to ultraviolet light, comprising the steps of:
preparing a water-in-oil-emulsion-type sunscreen product by stirring or agitating the sunscreen product precursor according to claim 43; and
applying the water-in-oil-emulsion-type sunscreen product to the human skin.

60. A method of reducing exposure of human skin to ultraviolet light, comprising the steps of:
preparing a water-in-oil-emulsion-type sunscreen product by stirring or agitating the sunscreen product precursor according to claim 44; and
applying the water-in-oil-emulsion-type sunscreen product to the human skin.

61. A method of reducing exposure of human skin to ultraviolet light, comprising the steps of:
preparing a water-in-oil-emulsion-type sunscreen product by stirring or agitating the sunscreen product precursor according to claim 45; and
applying the water-in-oil-emulsion-type sunscreen product to the human skin.

62. A method of reducing exposure of human skin to ultraviolet light, comprising the steps of:
preparing a water-in-oil-emulsion-type sunscreen product by stirring or agitating the sunscreen product precursor according to claim 46; and
applying the water-in-oil-emulsion-type sunscreen product to the human skin.

63. A method of reducing exposure of human skin to ultraviolet light, comprising the steps of:
preparing a water-in-oil-emulsion-type sunscreen product by stirring or agitating the sunscreen product precursor according to claim 47; and
applying the water-in-oil-emulsion-type sunscreen product to the human skin.

64. A method of reducing exposure of human skin to ultraviolet light, comprising the steps of:
preparing a water-in-oil-emulsion-type sunscreen product by stirring or agitating the sunscreen product precursor according to claim 48; and applying the water-in-oil-emulsion-type sunscreen product to the human skin.

\* \* \* \* \*